United States Patent [19]

Wustrow et al.

[11] Patent Number: 5,075,440

[45] Date of Patent: Dec. 24, 1991

[54] NOVEL PYRIDO(2,3-F)(1,4)THIAZEPINES AND PYRIDO(3,2-B)(1,5) BENZOTHIAZEPINES

[75] Inventors: David J. Wustrow, Ann Arbor, Mich.; Charles F. Schwender, Califon; John H. Dodd, Pittstown, both of N.J.

[73] Assignee: Ortho Pharmaceutical Corporation, Raritan, N.J.

[21] Appl. No.: 518,351

[22] Filed: May 3, 1990

[51] Int. Cl.$^5$ .................. C07D 281/18; C07D 281/10; C07D 281/12
[52] U.S. Cl. .................. 540/468; 540/548; 540/552
[58] Field of Search .............. 540/455, 547, 552, 468, 540/548; 514/211

[56] References Cited

U.S. PATENT DOCUMENTS 4,285,955  8/1981  Wehinger et al. .............. 546/258
4,532,248  7/1985  Franckowiak et al. .......... 514/211

OTHER PUBLICATIONS

Federsel et al., Tetrahedron Letters, vol. 21, 1980, pp. 2429-2432.
Pagani, J. Chem. Soc. Pepkins Trans. 11, 1974, pp. 1392-1397.

Primary Examiner—Mukund J. Shah
Assistant Examiner—E. C. Ward

[57] ABSTRACT

Novel pyrido[2,3-f] [1,4]thiazepines and novel pyrido[3,2-b] [1,5]benzothiazepines of the formula:

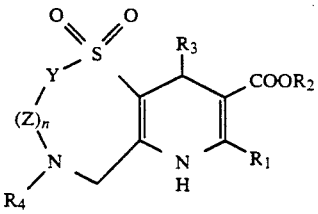

These compounds are useful as calcium channel antagonists with cardiovascular, antiasthmatic and antibronchoconstriction activity. Also described are methods of producing the novel compounds and intermediates thereof.

3 Claims, No Drawings

NOVEL PYRIDO[2,3-F](1,4)THIAZEPINES AND PYRIDO[3,2-B](1,5)BENZOTHIAZEPINES

BACKGROUND OF THE INVENTION

1. Field of the Invention

This invention relates to novel pyrido[2,3-f][1,4]-thiazepines and novel pyrido[3,2-b][1,5]benzothiazepines. These compounds are inhibitors of calcium ion uptake into smooth muscle tissue, and act to relax or prevent contraction of the tissue mediated by calcium mechanisms. The compounds are active antihypertensives and bronchodilators.

These compounds are useful for the treatment of cardiovascular disorders, including hypertension, ischemia, angina, congestive heart failure, migraine, myocardial infarction and stroke. The compounds are also useful for the treatment of other disorders such as hypersensitivity, allergy, asthma, dysmenorrhea, esophageal spasm, gastrointestinal motility disorders, glaucoma, premature labor and urinary tract disorders. The present invention also relates to a process for preparing these compounds, compositions thereof, methods of use and novel intermediates.

2. Related Disclosure

U.S. Pat. No. 4,285,955 and U.S. Pat. No. 4,483,985 (which is a divisional of the aforementioned patent) disclose acyclic sulfone substitution on simple dihydropyridines which possess calcium channel antagonist activity. However, the compounds in question are chemically distinct from the compounds of the present invention.

10-Phenyl-2H-thiopyrano[3,2-b]quinolines are disclosed in Pagani, G.P.A., *J. Chem. Soc.. Perkin Trans.* 2, 1392 (1974). However, these compounds are not calcium channel antagonists.

U.S. Pat. No. 4,532,248 discloses a broad genus of dihydropyridines, including cyclic sulfones fused to a dihydropyridine nucleus. Cardiotonic activity is claimed for the entire genus. The compounds of the present invention, on the other hand, are potent calcium antagonists with pharmacologic activity opposite to that claimed in U.S. Pat. No. 4,532,248.

SUMMARY OF THE INVENTION

The present invention is directed to pyrido[2,3-f][1,4]thiazepines and pyrido[3,2-b][1,5]benzothiazepines of the general formula

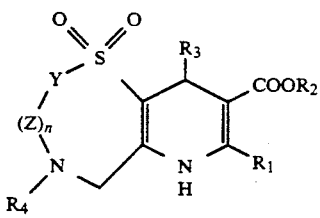

where

Y and Z may be $CH_2$, or together Y and Z may form a fused phenyl ring;

$R_1$ may be hydrogen, amino, $C_1$-$C_8$ straight or branched chain alkyl, trifluoromethyl or alkoxymethyl;

$R_2$ may be $C_1$-$C_8$ straight or branched chain alkyl, benzyl, 3-piperidyl, N-substituted 3-piperidyl, N-substituted 2-pyrrolidinyl methylene or substituted alkyl;

wherein said N-substituted 3-piperidyl and said N-substituted 2-pyrrolidinyl methylene may be substituted with $C_1$-$C_8$ straight or branched chain alkyl or benzyl, and said substituted alkyl may be substituted with $C_1$-$C_8$ alkoxy, $C_2$-$C_8$ alkanoyloxy, phenylacetyloxy, benzoyloxy, hydroxy, halogen, p-tosyloxy, mesyloxy, amino, carboalkoxy or $NR_5R_6$;

$R_3$ may be 2-pyridyl, 3-pyridyl, 2-thienyl, 3-thienyl, 2,1,3-benzoxadiazolyl, 2,1,3-benzthiadiazolyl or substituted phenyl;

wherein said substituted phenyl may be substituted at any of positions 2-6 with hydrogen, $C_1$-$C_8$ straight or branched chain alkyl, $C_1$-$C_8$ alkoxy, cyano, $C_1$-$C_4$ carboalkoxy, $C_1$-$C_8$ alkylthio, difluoromethoxy, difluoromethylthio, $C_1$-$C_8$ alkylsulfonyl, halogen, nitro or trifluoromethyl;

$R_4$ may be hydrogen, $C_1$-$C_8$ straight or branched chain alkyl, $C_3$-$C_7$ cycloalkyl, phenyl, benzyl, substituted benzyl, formyl, acetyl, t-butyloxy carbonyl, propionyl, substituted alkyl or $R_7CH_2C=O$;

wherein said substituted benzyl may be substituted with halogen, trifluoromethyl, $C_1$-$C_8$ straight or branched chain alkyl or $C_1$-$C_8$ alkoxy, and said substituted alkyl may be substituted with amino, $C_1$-$C_4$ dialkyl amino, $C_1$-$C_8$ alkoxy, hydroxy or halogen;

$R_5$ and $R_6$ may be the same or different and may be hydrogen, $C_1$-$C_8$ straight or branched chain alkyl, $C_3$-$C_7$ cycloalkyl, phenyl, benzyl, phenethyl or $R_5$ and $R_6$ together may form a heterocyclic ring selected from the group consisting of piperidino, pyrrolidino, morpholino, thiomorpholino, piperazino or an $N_4$-substituted derivative of piperidine;

wherein said N-substituted heterocyclic ring may be substituted with hydrogen, $C_1$-$C_8$ straight or branched chain alkyl, benzyl, benzhydryl, phenyl or substituted phenyl;

wherein said substituted phenyl may be substituted with hydrogen, $C_1$-$C_8$ alkoxy, halogen, $C_1$-$C_8$ straight or branched chain alkyl, nitro or trifluoromethyl;

$R_7$ may be amino, $C_1$-$C_4$ dialkyl amino, $C_1$-$C_8$ alkoxy, hydroxy or halogen;

n may be 1 to 4; and optical antipodes (enantiomers or diasteriomers) or pharmaceutically acceptable salts thereof such as salts of organic and inorganic acids such as hydrochloric, hydrobromic, fumaric, maleic, p-toluene sulfonic, methyl sulfonic acid and the like.

Also included in this invention is a process for preparing the compounds described above, said process disclosed in detail hereinafter. A further part of the present invention are certain intermediates and the process for the preparation thereof.

The compounds of the above formula inhibit the uptake of calcium ions into smooth muscle, and therefore act to relax or prevent calcium ion-mediated contraction of smooth muscle tissue. These compounds are useful for the treatment of cardiovascular disorders, including hypertension, ischemia, angina, congestive heart failure, myocardial infarction and stroke. The compounds are also useful for the treatment of other disorders such as hypersensitivity, allergy, asthma, bronchospasm, dysmenorrhea, esophageal spasm, gastrointestinal motility disorders, glaucoma, premature labor and urinary tract disorders.

DETAILED DESCRIPTION OF THE INVENTION

The invention in its broadest aspects relates to pyrido[2,3-f][1,4]thiazepines and pyrido[3,2-b][1,5]benzothiazepines which inhibit the uptake of calcium ions into smooth muscle tissue. The compounds which possess this activity are shown in the formula above.

The preferred compounds of the present invention are those in which $R_1$ is methyl;

$R_2$ is ethyl or substituted $C_1$-$C_8$ alkyl wherein the substituent is acetoxy, amino or $NR_5R_6$ wherein $R_5$ and $R_6$ are as previously defined;

$R_3$ is substituted phenyl;

$R_4$ is hydrogen, $C_1$-$C_8$ straight or branched chain alkyl, benzyl, formyl, $R_7CH_2C=O$ or t-butyloxy carbonyl;

$R_7$ is amino; and n is 1;

and the optical antipodes (enantiomers or diastereoisomers) or the pharmaceutically acceptable salts thereof.

Particularly, the preferred compounds of the present invention are:

1. 2-(N-benzyl-N-methylamino)ethyl 9-(2,3-dichlorophenyl)-1,1-dioxo-2,3,4,5,6,9-hexahydro-7-methyl-pyrido[2,3-f][1,4]thiazepine-8-carboxylate;
2. 2-(N-benzyl-N-methylamino)ethyl 9-(2,3-dichlorophenyl)-4,7-dimethyl-1,1-dioxo-2,3,4,5,6,9 -hexahydro-pyrido2,3-f][1,4]thiazepine-8-carboxylate;
3. Ethyl 9-(2,3-dichlorophenyl)-1,1-dioxo-2,3,4,5,6,9-hexahydro-7-methyl-pyrido[2,3-f][1,4]thiazepine-8-carboxylate;
4. Ethyl 9-(2,3-dichlorophenyl)-1,1-dioxo-4-ethyl-2,3,4,5,6,9-hexahydro-7-methyl-pyrido[2,3-f][1,4]-thiazepine-8-carboxylate;
5. Ethyl 9-(2,3-dichlorophenyl)-4,7-dimethy-1,1-dioxo-2,3,4,5,6,9-hexahydropyrido[2,3-f][1,4]thiazepine-8-carboxylate;
6. Ethyl 4,7-dimethyl-1,1-dioxo-2,3,4,5,6,9-hexahydro-9-(2,3,4,5,6-pentafluorophenyl)-pyrido[2,3-f][1,4]-thiazepine-8-carboxylate;
7. Ethyl 1,1-dioxo-2,3,4,5,6,9-hexahydro-7-methyl-9-(2,3,4,5,6-pentafluorophenyl)-pyrido[2,3-f][1,4]-thiazepine-8-carboxylate;
8. Ethyl 1,1-dioxo-4-ethyl-2,3,4,5,6,9-hexahydro-7-methyl-9-(3-nitrophenyl)-pyrido[2,3-f][1,4]-thiazepine-8-carboxylate;
9. Ethyl 4-(2,3-dichlorophenyl)-5,5-dioxo-10-formyl-2-methyl-1,4,10,11-tetrahydropyrido[3,2-b][1,5]-benzothiazepine-3-carboxylate;
10. 2-Acetoxyethyl 9-(2,3-dichlorophenyl)-4,7-dimethyl-1,1-dioxo-2,3,4,5,6,9-hexahydropyrido[2,3-f][1,4]-thiazepine-8-carboxylate;
11. 2-Pivaloyloxyethyl 9-(2,3-dichlorophenyl)-4,7-dimethyl-1,1-dioxo-2,3,4,5,6,9-hexahydropyrido[2,3-f][1,4]thiazepine-8-carboxylate;
12. Ethyl 4-(2,3-dichlorophenyl)-2,10-dimethyl-5,5-dioxo-1,4,10,11-tetrahydropyrido[3,2-b][1,5]-benzothia-zepine-3-carboxylate;
13. 2-(N-benzyl-N-methylamino)ethyl 4-(2,3-dichlorophenyl)-2,10-dimethyl-5,5-dioxo-1,4,10,11-tetrahydropyrido[3,2-b][1,5]benzothiazepine-3-carboxylate;
14. 2-(N,N-dibenzylamino)ethyl 4-(2,3-dichlorophenyl)-4,7-dimethyl-1,1-dioxo-2,3,4,5,6,9-hexahydropyrido[2,3-f][1,4]thiazepine-8-carboxylate;
15. 2-(N-benzyl-N-methylamino)ethyl 4-(2,3-dichlorophenyl)-4-ethyl-1,1-dioxo-2,3,4,5,6,9-hexahydro-7-methyl-pyrido[2,3-f][1,4]thiazepine-8-carboxylate; and
16. (N-benzyl-2-pyrolidinyl)methyl 9-(2,3-dichlorophenyl)-4,7-dimethyl-1,1-dioxo-2,3,4,5,6,9-hexahydropyrido[2,3-f][1,4]thiazepine-8-carboxylate.

The compounds of the present invention in which Y and Z are $CH_2$ (i.e. pyrido[2,3-f][1,4]thiazepines) are prepared as shown in Scheme I below.

SCHEME 1

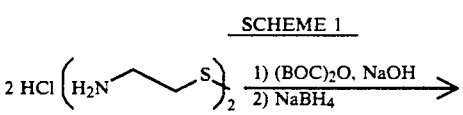

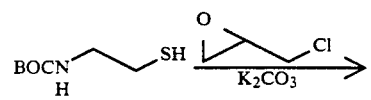

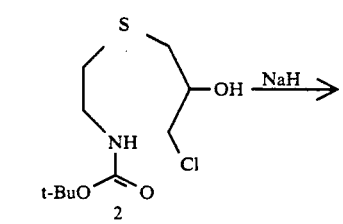

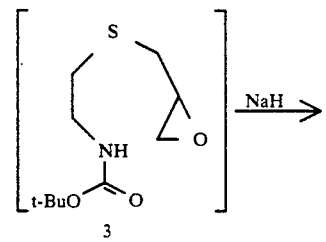

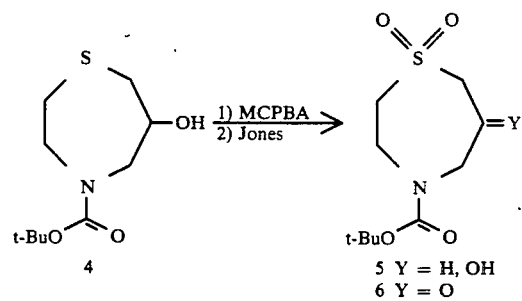

5 Y = H, OH
6 Y = O

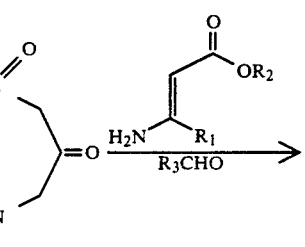

6 $R_4$ = BOC

-continued
SCHEME 1

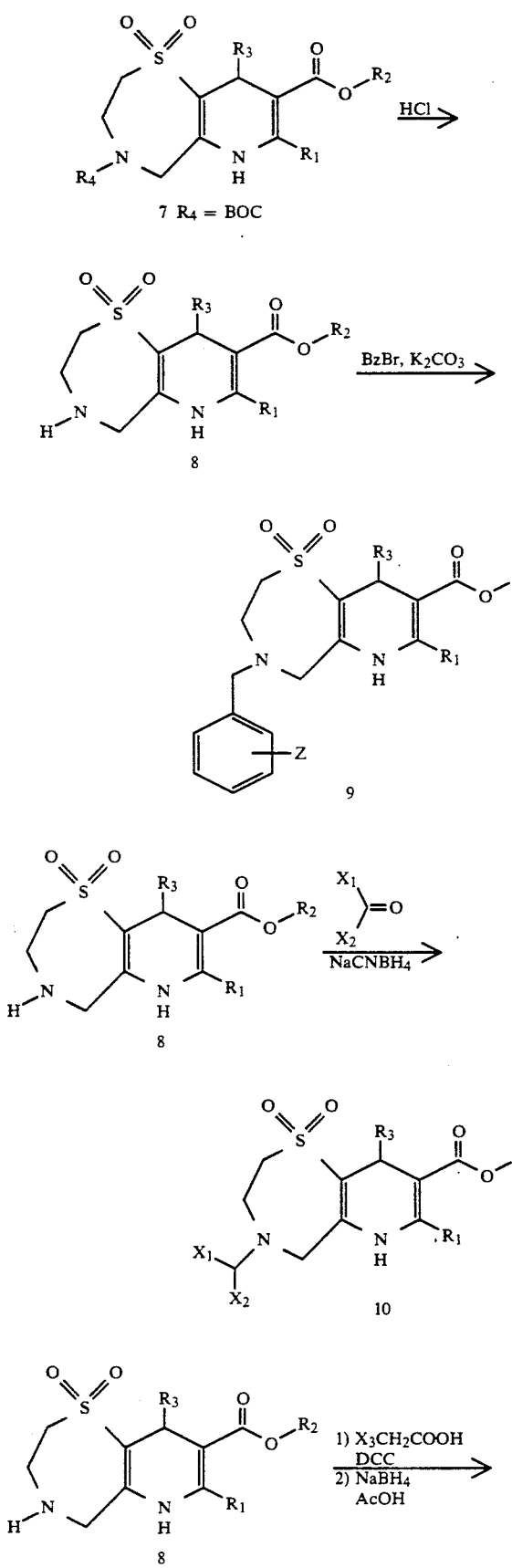

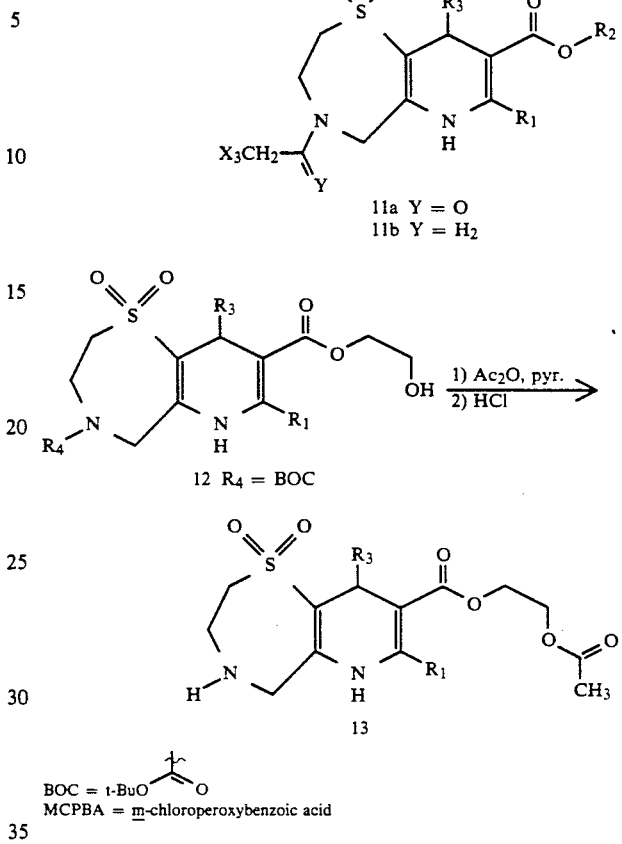

BOC = t-BuO-C(=O)-O
MCPBA = m-chloroperoxybenzoic acid

The thiazepinone (6) is a key intermediate in the synthesis of some dihydropyridines and was prepared in the following manner. Reaction of the BOC protected cystamine (1) (available in two steps as shown above, and described in Examples 1 and 2) with epichlorohydrin followed by cyclization of the intermediate chlorohydrin (2) resulted in thiazepinol (4). Cyclization of chlorohydrin (2) proceeds through epoxide (3). Nucleophilic attack by the carbamate anion opens the epoxide from the less hindered side resulting in formation of the thiazepinol (4). The intermediate epoxide (3) can be isolated if only 1 equivalent of base is used, or the chlorohydrin (2) can be cyclized directly to (4) by the addition of 2 equivalents of base. Thiazepinol (4) was oxidized first with m-chloroperoxybenzoic acid to obtain 1,1-dioxo-thiazepinol (5) which was then oxidized with Jones reagent to obtain the 1,1-dioxothiazepinone (6).

The ketosulfone (6) was then reacted with an appropriately substituted aldehyde and substituted 3-aminoacrylate derivatives to obtain the dihydropyridines (7). The t-butyloxy protecting group was removed by exposure of the dihydropyridine (7) to acidic conditions to yield (8). The free amino functionality of (8) can then be alkylated by benzyl bromide or substituted benzyl bromides to give (9) (where Z=halo, alkyl alkyloxy, alkoxy, nitro, or trifluoromethyl), or reductively aminated with aldehydes or ketones to give (10) (where $X_1$ and $X_2$ are hydrogen, alkyl, cycloalkyl or together form a homocyclic or heterocylic ring). Additionally, the amine (8) can be acylated using various carboxylic acids (where $X_3$ is hydrogen, alkyl, amino, disubstituted amino, alkoxy, hydroxy or halogen) to give the amides (11a) which can then be reduced to the corresponding amines (11b). In the case where an alkoxy group is present on the ester side chain as in (12), it can be acylated and the t-BOC protecting group can be removed to give the compound (13) which can be benzylated, alkylated or acylated in a manner analogous to (8).

The compounds of the present invention in which Y and Z together form a phenyl ring (i.e. pyrido[3,2-b][1,5]benzothiazepines) are prepared as shown in Scheme 2 below.

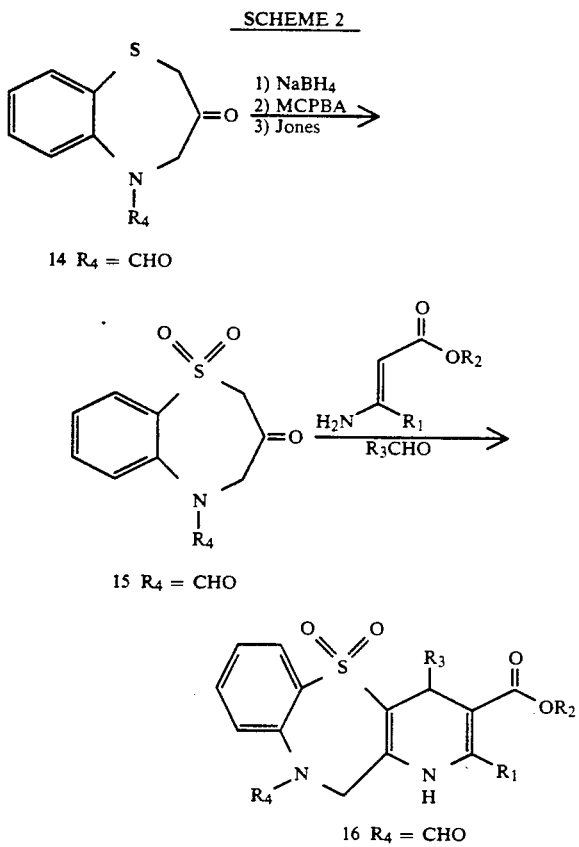

1,1-Dioxo-benzothiazepenone (15) is prepared in three steps from known benzothiazepinone (14) as shown and as described by Federsel, H. J. et al., *Tetrahedron Letters* 21, 2229 (1986). The dihydropyridine (16) is prepared by reacting (15) with the appropriate aldehyde and substituted 3-aminoacrylate.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The compounds may also be administered in the form of an aerosol. The pharmaceutical compositions will generally contain per dosage unit, e.g., tablet, capsule, powder, injection, teaspoonful and the like, from about 0.001 to about 100 mg/kg, and preferably from about 0.001 to about 20 mg/kg of the active ingredient.

The following examples describe the invention in greater particularity and are intended to illustrate but not limit the invention.

EXAMPLE 1

Bis-N-(t-Butyloxycarbonyl)-cystamine

A mixture of cystamine dihydrochloride (46.95 g, 0.285 moles) in 1 L THF and sodium hydroxide (33.33 g, 0.833 mole) in 500 mL of water was treated with di-t-butyldicarbonate (100.0 g, 0.458 mole) and stirred at room temperature for 2 hours. The aqueous phase was separated and extracted with 2×500 mL of ether. The combined organic phases were dried with brine and $MgSO_4$ and evaporated under reduced pressure to afford the product as a white solid (78.2 g, 78% yield) D.C.I.M.S. (M+H) 325.

EXAMPLE 2

N-(t-Butyloxycarbonyl)-2-aminoethanethiol

A solution of bis N-(t-butyloxycarbonyl)-cystamine (77.37 g, 0.220 mole) from Example 1, in 1 L of ethanol was treated with $NaBH_4$ (32.5 g, 0.859 mmole). Vigorous gas evolution ensued and subsided in 40 minutes. The reaction was stirred for an additional half hour and was poured into 2.5 L of a cold dilute solution of citric acid (pH 6). The mixture was then extracted with 3×1 L of chloroform. The combined organic extracts were dried with $MgSO_4$ and the solvents were removed under reduced pressure. The resulting residue was distilled (66°-73° C. 0.25 torr) to obtain the product (41.5 g, 53% yield).

EXAMPLE 3

(2-(t-Butyloxycarbonyl-amino)-ethyl)
-(3-chloro-2-hydroxypropyl)-thioether

N-(t-butyloxycarbonyl)-aminoethanethiol (40 g, 225 mmole) from Example 2, and epichlorohydrin (35.4 g, 383 mmole) in 300 mL of ethanol were cooled to 0° C. and treated with potassium carbonate (35.4 g). The reaction was warmed to room temperature over 90 minutes and filtered through celite. The volatiles were removed under reduced pressure to give a clear oil (62.09 g, 100% yield) D.C.I.M.S. 270(M+H).

EXAMPLE 4

4-N-(t-Butyloxycarbonyl)-6-hydroxy
-2,3,4,5,6,7-hexahydro-1,4-thiazepine (2-(t-Butyloxycarbonyl-amino)-ethyl)-(3-chloro-2-hydroxypropyl)-thioether (30 g, 111.52 mmole) from Example 3, was dissolved in dimethylformamide (500 mL) at 0° C. and treated with sodium hydride (9.81 g, 245 mmole) in 3 portions over 15 minutes. The reaction was allowed to warm to room temperature over 1 hour and 15 minutes, poured into 2.5 L ice water and extracted with 3×1 L chloroform. The combined organic extracts were dried with brine and Na$_2$SO$_4$, evaporated, and the resulting residue chromatographed (3:1 hexane:ethyl acetate, silica gel) to obtain the product as a white solid (12.47 g, 48% yield) D.C.I.M.S. 234(M+H) M.P. 80°-82° C.

EXAMPLE 5

4-N-(t-Butyloxycarbonyl)-1,1-dioxo-6-hydroxy-2,3,4,5,6,7-hexahydro-1,4-thiazepine A solution of 4-N-(t-butyloxycarbonyl)-6-hydroxy-2,3,4,5,6,7-hexahydro-1,4-thiazepine (11.7 g, 50.6 mmole) from Example 4, in 100 mL of chloroform was added in a dropwise manner to a solution of m-chloroperbenzoic acid (19.2 g, 111 mmole) in chloroform (130 mL) over 1 hour. After the addition was complete, the reaction was stirred at ambient temperature for 2 hours. The reaction mixture was filtered and the filtrate concentrated under reduced pressure. The resulting residue was recrystallized from ethyl acetate-hexane to give the product (11.37 g, 85%) D.C.I.M.S. 266(M+H) M.P. 123°-124° C.

EXAMPLE 6

4-N-(t-Butyloxycarbonyl)-1,1-dioxo-2,3,4,5,6,7-hexahydro-1,4-thiazepin-6-one

4-N-(t-Butyloxycarbonyl)-1,1-dioxo-6-hydroxy-2,3,4,5,6,7-hexahydro-1,4-thiazepine (10.0 g, 37.7 mmole) from Example 5, was dissolved in 110 mL of acetone, cooled to 0° C. and treated with 18.8 mL of freshly prepared Jones reagent. The reaction was stirred at ambient temperature for three hours and then treated with 5 mL of methanol. After 15 minutes, the reaction was filtered through magnesium sulfate and the filtrate immediately concentrated. The residue was filtered through a pad of silica gel using 3:1 chloroform-ethyl acetate to obtain the produce (9.67 g, 87%) D.C.I.M.S. 264(M+H) M.P. 172°-173° C.

EXAMPLE 7

Ethyl 9-(2,3-Dichlorophenyl)-4-(t-butyloxycarbonyl)-1,1-dioxo-2,3,4,5,6,9-hexahydro-7-methylpyrido[2,3-f][1,4]thiazepine-8-carboxylate A mixture of 4-N-(t-butyloxycarbonyl)-1,1-dioxo-2,3,4,5,6,7-hexahydro-1,4-thiazepin-6-one (2.00 g, 7.60 mmole) from Example 6, 2,3-dichlorobenzaldehyde (1.33 g, 7.60 mmole) and ethyl 3-aminocrotonate (0.98 g, 7.60 mmole) was heated to reflux in 40 mL of ethanol for 24 hours. The ethanol was removed under reduced pressure and replaced with 85 mL of toluene. The mixture was heated to reflux for 2 hours, cooled to room temperature and filtered to obtain the produce (2.45 g, 61%).

EXAMPLE 8

Ethyl 9-(2,3-Dichlorophenyl)-1,1-dioxo-2,3,4,5,6,9-hexahydro-7-methylpyrido-[2,3-f][1,4]thiazepine-8-carboxylate A mixture of ethyl 9-(2,3-dichlorophenyl)-4-(t-butyloxycarbonyl)-1,1-dioxo-2,3,4,5,6,9-hexahydro-7-methylpyrido[2,3-f][1,4]thiazepine-8-carboxylate (2.45 g, 4.6 mmole) from Example 7, in ethyl acetate (150 mL) was cooled to 0° C. and saturated with gaseous hydrogen chloride. The mixture was warmed to room temperature. The reaction was then again chilled to 0° C. and shaken with 200 mL of cold 4 N NaOH. The aqueous layer was separated and extracted with 2×100 mL of chloroform. The ethyl acetate layer was dried with brine and the combined organic extracts were dried over Na$_2$SO$_4$. The solvents were evaporated under reduced pressure and the residue triturated with ether to give the product (1.86 g, 94% yield).

EXAMPLE 9

Ethyl 9-(2,3-Dichlorophenyl)-4,7-dimethyl-1,1-dioxo-2,3,4,5,6,9-hexahydropyrido-[2.3-f][1.41thiazepine-8-carboxylate A mixture of ethyl 9-(2,3-dichlorophenyl)-1,1-dioxo-2,3,4,5,6,9-hexahydro-7-methylpyrido-[2,3-f][1,4]thiazepine-8-carboxylate (0.500 g, 1.16 mmole) from Example 8, in acetonitrile (10 mL) was treated with formaldehyde (0.240 g, 37% aqueous solution) and sodium cyanoborohydride (0.062 g, 1.16 mmole). After 15 minutes, 6 drops of AcOH were added and the reaction was stirred for 1 hour. Then, 30 mL of water were added and the reaction mixture was extracted with 3×40 mL of chloroform. The pH was adjusted to 8 after the first extract. The combined organic extracts were dried with brine and Na$_2$SO$_4$ and then treated with 3 mL of triethylamine. After standing for 1.5 hours, the volatiles were removed under reduced pressure and the residue chromatographed (silica gel, 1.5% MeOH, 0.1% NH$_3$ in CHCl$_3$) to obtain the product as an oil which solidified on triturating with ether (0.479 g, 92% yield).

EXAMPLE 10

Ethyl 4-N-Benzyl-9-(2,3-dichlorophenyl)-1,1-dioxo-2,3,4,5,6,9-hexahydro-7-methylpyrido[2,3-f][1,4]thiazepine-8-carboxylate A mixture of ethyl 9-(2,3-dichlorophenyl)-1,1-dioxo-2,3,4,5,6,9-hexahydro-7-methylpyrido[2,3-f][1,4]-thiazepine-8-carboxylate (0.400 g, 0.92 mmole), benzyl bromide (0.190 g, 1.11 mmole), and potassium carbonate (0.213 g, 1.55 mmole) was heated in acetonitrile (10 mL) for 3 hours. The reaction was cooled, the solids filtered, and the solvent was evaporated under reduced pressure. The residue was then chromatographed (silica gel 2:1 hexane:ethyl acetate) to give the product which was crystallized from ether (0.313 g, 65% yield).

EXAMPLE 11

2-(N-benzyl-N-methylamino)ethyl 4-t-butyloxycarbonyl-9-(2,3-dichlorophenyl)-1,1-dioxo-5a-hydroxy-2,3,4,5,5a,6,9,9a-octahydro-7-methyl-pyrido[2,3-f][1,4]thiazepine-8-carboxylate A mixture of 4-N-(t-butyloxycarbonyl)-1,1-dioxo-2,3,4,5,6,7-hexahydro-1,4-thiazepin-6-one (8.39 g, 31.9 mmole) from Example 6, 2,3-dichlorobenzaldehyde (5.58 g, 31.9 mmole) and 2-(N-benzyl-N-methylamino)ethyl 3-aminocrotonate (7.91 31.9 mmole) were heated to reflux in 40 mL of ethanol for 17 hours. The reaction was cooled to room temperature, filtered, and the solid washed with 50 mL of ether to obtain the title compound (10.72 g, 50% yield) D.C.I.M.S. (M+H) 668.

EXAMPLE 12

2-(N-Benzyl-N-methylamino)ethyl 9-(2,3-dichlorophenyl)-4,7-dimethyl-1,1-dioxo-5a-hydroxy-2,3,4,5,6,9-hexahydro-7-pyrido-[2,3-f][1,4thiazepine-8-carboxylate 4-N-(t-Butyloxycarbonyl)-1,1-dioxo-2,3,4,5,6,7-hexahydro-1,4-thiazepin-6-one (2.10 g, 3.2 mmole) from Example 6, was treated as in Examples 8 and 9 to obtain the product which was recrystallized from isopropanol (1.23 g, 70% yield).

EXAMPLE 13

Optical Resolution of Ethyl 9-(2,3-dichlorophenyl)-1,1-dioxo-2,3,4,5,6,9-hexahydro-7-methylpyrido[2,3-f][1,4]-thiazepine-8-carboxylate Racemic ethyl 9-(2,3-dichlorophenyl)-1,1-dioxo-2,3,4,5,6,9-hexahydro-7-methylpyrido[2,3-f][1,4]-thiazepine-8-carboxylate (2.41 g, 5.59 mmole) from Example 8, was dissolved in 100 mL of hot methanol. This solution was combined with D-dibenzoyl tartrate (2.10 g, 5.59 mmole), and the solvent was removed under reduced pressure. The residue was crystallized 3 times from ethyl acetate. The salt was converted to the free base by extraction of a chloroform solution of the salt with aqueous ammonia. $[\alpha]^D = +7.7°$ (C, 0.41, CHCl$_3$). The (−) isomer was obtained in a similar fashion using L-dibenzoyl tartaric acid; $[\alpha]^D = -8.0$ (C, 0.40, CHCl$_3$).

EXAMPLE 14

5-N-Formyl-3-hydroxy-2,3,4,5-tetrahydro-[1,5]-benzothiazepine

To a solution of 5-N-formyl-3-hydroxy-2,3,4,5-tetrahydro-[1,5]-benzothiazepin-3-one (0.480 g, 2.31 mmole) prepared as described by Federsel, H. J. et al., *Tetrahedron Letters* 21, 2229 (1986), in 10 mL of ethanol was added NaBH$_4$ (0.090 g, 2.38 mmole). The reaction was stirred at room temperature for 1 hour. The reaction was partitioned between a saturated NH$_4$Cl solution and chloroform. The organic layer was washed with water, brine and dried over MgSO$_4$. The solvents were removed under reduced pressure to give the product as an oil (0.452 g, 94% yield) D.C.I.M.S. 210 [M+H].

EXAMPLE 15

1,1-Dioxo-5-N-formyl-3-hydroxy-2,3,4,5-tetrahydro-[1,5]-benzothiazepine

A solution of m-chloroperoxybenzoic acid (0.946 g, 5.5 mmole) in 20 ml of chloroform was treated with 5-N-formyl-3-hydroxy-2,3,4,5-tetrahydro-[1,5]-benzothiazepine (0.450 g, 1.93 mmole) from Example 14, in 10 mL of chloroform. The reaction was stirred for 16 hours at room temperature and the solvents were removed under reduced pressure. The residue was triturated with 2×10 mL water and the water was evaporated to obtain the product (0.443 g, 95% yield) D.C.I.M.S. 242 [M+H].

EXAMPLE 16

1,1-Dioxo-5-N-formyl-2,3,4,5-tetrahydro-[1,5]-benzothiazepine-3-one

A solution of 1,1-dioxo-5-N-formyl-3-hydroxy-2,3,4,5-tetrahydro-[1,5]-benzothiazepine (0.443 g, 1.83 mmole) from Example 15, in 5 mL of acetone was treated with Jones reagent (0.54 mL, 1.40 mmole), and the solution was heated to reflux for 15 minutes. An additional 0.15 mL of Jones reagent was added and the reaction was heated for 20 minutes longer. The cooled solution was filtered through MgSO$_4$, and the solvents were removed under reduced pressure. The residue was triturated with chloroform and filtered. Evaporation of the filtrate afforded the product (0.418 g, 95% yield) D.C.I.M.S. 240 [M+H].

EXAMPLE 17

Ethyl 4-(2,3-Dichlorophenyl)-5,5-dioxo-10-formyl-2-methyl-1,4,10,11-tetrahydropyrido[3,2-b][1,5]-benzothiazepine-3-carboxylate A solution of 1,1-dioxo-5-N-formyl-2,3,4,5-tetrahydro-[1,5]-benzothiazepin-3-one (0.410 g, 1.71 mmole) from Example 16, 2,3-dichlorobenzaldehyde (0.297 g, 1.71 mmole) and ethyl 3-aminocrotonate (0.219 g, 1.71 mmole) in 7 mL of ethanol was heated to reflux for 18 hours. The solvent was removed under reduced pressure and the residue was chromatographed (silica gel, 1:1 hexane:ethyl acetate) to obtain the product as an oil (0.75 g, 86% yield). The product was recrystallized from chloroform-ether.

EXAMPLE 18

2-Hydroxyethyl 4-t-Butyloxycarbonyl-9-(2,3-dichlorophenyl)-1,1-dioxo-5a-hydroxy-2,3,4,5,5a,6,9,9a-octahydro-7-methylpyrido-[2,3-f][1,4]thiazepine-8-carboxylate A mixture of 4-N-(t-butyloxycarbonyl)-1,1-dioxo-2,3,4,5,6,7-hexahydro-1,4-thiazepine-6-one (9.06 g, 34.5 mmole) from Example 6, 2,3-dichlorobenzaldehyde (6.03 g, 34.5 mmole) and 2-hydroxyethyl 3-aminocrotonate (5.00 g, 34.5 mmole) was heated to reflux in 200 mL of ethanol for 24 hours. The ethanol was removed under reduced pressure and the residue was heated in refluxing toluene for 2 hours. After cooling a precipitate was filtered to give 6.75 g of the title compound. Evaporation of the filtrate and chromatography (2.5:1, ethyl acetate:hexane) produced 3.78 g of product.

EXAMPLE 19

2-Acetoxyethyl 9-(2,3-Dichlorophenyl)-1,1-dioxo-2,3,4,5,6,9-hexahydro-7-methylpyrido [2,3-f][1,4]thiazepine-8-carboxylate 2-Hydroxyethyl 4-t-butyloxycarbonyl-9-(2,3-dichlorophenyl)-1,1-dioxo-5a-hydroxy-2,3,4,5,5a,6,9,9a-octahydro-7-methylpyrido[2,3-f][1,4]thiazepine-8-carboxylate (0.500 g, 0.97 mmole) from Example 18, was dissolved in 5 mL of pyridine and 5mL of acetic anhydride, and stirred for 2 hours. The solvents were removed under reduced pressure, and the residue was slurried in 25 mL of ethyl acetate and cooled to 0° C., after which the mixture was saturated with gaseous HCl. After 90 minutes, the reaction was poured into 30 mL of 4N NaOH. The ethyl acetate layer was separated and dried with brine, and the aqueous layer was extracted with 2×30 mL of chloroform. The combined organic extracts were dried with sodium sulfate and evaporated, and the residue was chromatographed (2% methanol, 0.1% ammonia in chloroform, silica gel) to give the product as a white solid (0.351 g, 89% yield).

EXAMPLE 20

2-Acetoxyethyl 9-(2,3-Dichlorophenyl)-4,7-dimethyl-1,1-dioxo-2,3,4,5,6,9-hexahydropyrido[2,3-f][1,4]thiazepine-8-carboxylate A mixture of 2-acetoxyethyl 9-(2,3-dichlorophenyl)-1,1-dioxo-2,3,4,5,6,9-hexahydro-7-methyl-pyrido[2,3-f][1,4]thiazepine-8-carboxylate (0.880 g, 1.69 mmole) from Example 19, and 1 mL of 38% aqueous formaldehyde solution in 20 mL of acetonitrile was treated with sodium cyanoborohydride (0.070 g, 1.69 mmole). After stirring for 1 hour, 0.5 mL of acetic acid was added, and the reaction was stirred for another 2 hours. After the addition of 40 mL of water and adjustment of the pH to 9 with 6N sodium hydroxide, the reaction was extracted with 3×30 mL of chloroform. The combined organic extracts were dried with sodium sulfate, the solvent was removed under reduced pressure, and the residue was chromatographed (2% methanol, 0.1% ammonia in chloroform on silica gel) to obtain the title compound (0.743 g, 82%).

The physical constants for these dihydropyridine examples as well as a number of additional representative compounds of the present invention are presented below in Table 1.

TABLE 1

Additional Representative Compounds

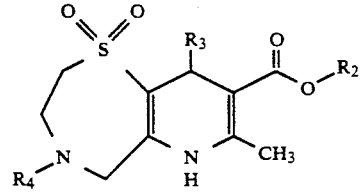

| $R_3$ = Phenyl Substitution | $R_4$ | $R_2$ | Molecular Formula | D.C.I.M.S. [M + H] | M.P. °C. |
|---|---|---|---|---|---|
| 2,3-dichloro | H | ethyl | $C_{18}H_{20}Cl_2N_2O_4S \cdot HCl \cdot 3/2\ H_2O$ | 431 | 145–7 |
| 2,3-dichloro | BOC | ethyl | $C_{23}H_{28}Cl_2N_2O_4S$ | 531 | 228–30 |
| pentafluoro | BOC | ethyl | $C_{23}H_{25}F_5N_2O_4S$ | 553 | 224–6 |
| 2,3-dichloro | Bz | ethyl | $C_{25}H_{26}Cl_2N_2O_4S$ | 521 | 219 (d) |
| pentafluoro | H | ethyl | $C_{18}H_{17}F_5N_2O_4S$ | 453 | 211–3 |
| 2,3-dichloro | Me | ethyl | $C_{19}H_{22}Cl_2N_2O_4S$ | 445 | 206–8 |
| 2-$CF_3$ | BOC | ethyl | $C_{25}H_{29}F_3N_2O_6S$ | 531 | 213–5 |
| 2-$CF_3$ | H | ethyl | $C_{19}H_{21}F_3N_2O_4S$ | 431 | 125 (d) |
| pentafluoro | Me | ethyl | $C_{19}H_{19}F_5N_2O_4S$ | 467 | 212–5 |
| 2,3-dichloro | CHO | ethyl | $C_{23}H_{20}Cl_2N_2O_5S$* | 507 | 185–7 |
| 2,3-dichloro | Et | ethyl | $C_{20}H_{24}Cl_2N_2O_4S \cdot HCl \cdot 3/2\ H_2O$ | 459 | 185–8 |
| 2-Cl, 6-F | H | ethyl | $C_{18}H_{20}ClFN_2O_4S$ | 415 | 118–20 |
| 3-nitro | H | ethyl | $C_{18}H_{21}N_3O_6S$ | 408 | 186–8 |
| 2,3-dichloro | Pr | ethyl | $C_{21}H_{26}Cl_2N_2O_4S$ | 473 | 196–8 |
| 2-nitro | H | ethyl | $C_{18}H_{21}N_3O_6S$ | 408 | 171–3 |
| 2,3-dichloro | iPr | ethyl | $C_{21}H_{28}Cl_2N_2O_4S$ | 473 | 217–8 |
| 2,3,-dichloro | heptyl | ethyl | $C_{25}H_{34}Cl_2N_2O_4S$ | 529 | 142–4 |
| 2,3-(213 oxadialzolyl) | H | ethyl | $C_{18}H_{20}N_4O_5S \cdot HCl$ | 405 | 216–9 |
| 3-nitro | Et | ethyl | $C_{20}H_{25}N_2O_6S \cdot HCl \cdot 3/2\ H_2O$ | 436 | 195 (d) |
| 2,3-dichloro | H | ethyl | $C_{18}H_{20}Cl_2N_2O_4S$ (−) | 431 | 190 (d) |
| 2,3-dichloro | H | ethyl | $C_{18}H_{20}Cl_2N_2O_4S$ (+) | 431 | 193 (d) |
| 2,3-dichloro | $NH_2CH_2CO$ | ethyl | $C_{20}H_{23}Cl_2N_3O_5S$ | 488 | 166 (d) |
| 2,3-dichloro | H | N—Bz—N—Me-ethyl | $C_{26}H_{29}N_3O_4Cl_2S$ | 550 | 132–5 |
| 2,3-dichloro | Me | N—Bz—N—Me-ethyl | $C_{27}H_{31}N_3O_4Cl_2S$ | 564 | 166–8 |
| 2,3-dichloro | Me | N—Bz—N—Me-ethyl | $C_{27}H_{31}N_3O_4Cl_2S \cdot 2HCl \cdot H_2O$ | 564 | 173 (d) |
| 2,3-dichloro | Me | 2-acetoxy-ethyl | $C_{21}H_{24}Cl_2N_2O_6S$ | 503 | 168–70 |
| 2,3-dichloro | Me | 2-hydroxy-ethyl | $C_{19}H_{22}Cl_2N_2O_5S$ | 461 | 203–4 |
| 2,3-dichloro | H | 2-acetoxy-ethyl | $C_{20}H_{24}Cl_2N_2O_6S$ | 489 | 179–81 |
| 2,3-dichloro | H | 2-hydroxy-ethyl | $C_{18}H_{20}Cl_2N_2O_5S$ | 447 | 197–9 |
| 2,3-dichloro | H | cyclopropylmethyl | $C_{20}H_{22}Cl_2N_2O_4S$ | 457 | 199–200 |
| 2,3-dichloro | H | cyclopropylmethyl | $C_{21}H_{24}Cl_2N_2O_4S$ | 471 | 177–9 |
| 2,3-dichloro | H | 2-i-butryloxy ethyl | $C_{23}H_{28}Cl_2N_2O_6S$ | 531 | 185–5 |
| 2,3-dichloro | Me | 2-benzoyloxy-ethyl | $C_{26}H_{26}Cl_2N_2O_6S$ | 565 | 108–10 |
| 2,3-dichloro | Et | 2-NBz(Me)-ethyl | $C_{28}H_{33}Cl_2N_3O_4S \cdot 2HCl \cdot H_2O$ | 578 | 171–3 |
| 3-nitro | Me | 2-NBz(Me)-ethyl | $C_{27}H_{32}Cl_2N_4O_6S \cdot 2HCl \cdot H_2O$ | 541 | 148 (d) |
| 2,3-dichloro | Me | 2-$NBz_2$-ethyl | $C_{33}H_{35}Cl_2N_3O_4S \cdot 2HCl \cdot H_2O$ | 640 | 175 (d) |
| 2,3-dichloro | Me | 3-Ph-propyl | $C_{33}H_{35}Cl_2N_3O_4S \cdot HCl$ | 535 | 173 (d) |
| 2-chloro-3-$NO_2$ | Me | ethyl | $C_{19}H_{23}ClN_2O_4S$ | 456 | 199–201 |
| 2,3-dichloro | i-Pr | 2-acetoxyethyl | $C_{23}H_{28}Cl_2N_2O_6S$ | 531 | 181–3 |
| 2,3-dichloro | Et | 2-acetoxyethyl | $C_{22}H_{26}Cl_2N_2O_6S$ | 517 | 187–9 |
| 2,3-dichloro | Bz+ | 2-acetoxyethyl | $C_{27}H_{28}Cl_2N_2O_6S$ | 579 | 102–4 |
| 2-chloro | Me | ethyl | $C_{19}H_{23}ClN_2O_4S$ | 411 | 223–4 |

*Benzothiazepine ring system
+Bz = benzyl

Table 2, below, sets forth inhibition of nitrendipine binding as well as inhibition of calcium dependent smooth muscle contraction in terms of percent inhibition, for a number of representative compounds of the present invention.

TABLE 2

Calcium Channel Antagonist Activity $R_3$ = Phenyl

Structure (top):

A dihydropyridine with $R_3$ on phenyl substitution, $R_2$ as ester group, $R_4$-N-CH2-CH2-SO2- attached, and CH3/NH on the pyridine ring.

| R3 = Phenyl Substitution | R4 | R2 | P#166 Nit. Binding | P#176 Trach % INHB/μM | P#176 Aorta % INHB/μM |
|---|---|---|---|---|---|
| 2,3-dichloro | H | ethyl | 99, 105 nM | 73/1.0; 43/0.1 | 96/1.0; 85/0.1; 21/0.01 |
| 2,3-dichloro | BOC | ethyl | 32% @ 1.0 μM | 0/2.0 | 18/1.0; 4/0.3 |
| pentafluoro | BOC | ethyl | 24% @ 1 μM | 7/2.0 | 37/1.0; 0/0.1 |
| 2,3-dichloro | Bz | ethyl | 210 nM | 32/2.0; 10/0.1 | 79/1.0 |
| pentafluoro | H | ethyl | 90 nM | 98/2.0; 63/0.1; 13/0.01 | 95/1.0; 89/0.1; 61/0.01 |
| 2,3-dichloro | Me | ethyl | 120 nM | 98/2.0; 80/0.1; 55/0.01 | 97/1.0; 96/0.1; 67/0.01 |
| 2-CF3 | BOC | ethyl | 7% @ 1.0 μM | 50/2.0; 24/0.3 | 47/1.0; 37/0.1 |
| 2-CF3 | H | ethyl | 360 nM | 73/2.0; 35/0.3; 38/0.1 | 83/1.0; 68/0.1; 37/0.01 |
| pentafluoro | Me | ethyl | 53 nM | 95/1.0; 73/0.1; 35/0.01 | 97/1.0; 50/0.01 |
| 2,3-dichloro | Et | ethyl | 60 nM | 90/1.0; 70/0.3; 33/0.01 | 96/1.0; 76/0.1; 19/0.01 |
| 2-Cl, 6-F | H | ethyl | 870 nM | 88/2.0; 56/0.3 | 86/1.0; 4.8/0.01 |
| 3-nitro | H | ethyl | 240 nM | 93/2.0; 58/0.03 | 100/1.0; 88/0.1; |
| 2,3-dichloro | Pr | ethyl | 145 nM | 68/2.0; 53/0.3; 44/0.1; 30/0.03 | 100/1.0; 88/0.1; 53/0.01 |
| 2-nitro | H | ethyl |  | 75/2.0; 45/0.3; 12/0.10 | 77/1.0; 47/0.1; 27/0.01 |
| 2,3-dichloro | iPr | ethyl | 72 nM | 86/2.0; 61/0.3; 37/0.1 | 95/1.0; 83/0.1; 38/0.01 |
| 2,3-dichloro | hept | ethyl |  | 27/2.0 | 44.1.0; 4/0.1 |
| 2,3-(2,1,3 oxadiazolyl) | H | ethyl | 660 nM | 68/2.0; 22/0.3 | 83/1.0; 22/0.1 |
| 3-nitro | Et | ethyl |  | 92/0.3; 73/0.1; 50/0.03 | 73/0.10; 5/0.01 |
| 2,3-dichloro | H | ethyl |  | 54/2.0; 24/0.3; 2/0.1 | 69/1.0; 0/0.1; 0/.01 |
| 2,3-dichloro | H | ethyl |  | 96/2.0; 47/0.1; 25/0.03 | 97/1.0; 67/0.1; 14/0.01 |
| 2,3-dichloro | NH2CH2CO | ethyl |  | 36/2.0; 6/0.3 | 20/1.0 |
| 2,3-dichloro | H | N—Bz—N—Me-ethyl | 380 nM | 86/2.0; 62/0.3; 23/0.1 | 93/1.0; 48/0.1; 20/0.03 |
| 2,3-dichloro | Me | N—Bz—N—Me-ethyl | 150 nM | 88/2.0; 71/0.3; 54/0.1; 28/0.03 |  |
| 2,3-dichloro | Me | 2-acetoxyethyl |  |  | 89/1.0; 26/0.1; 0/0.01 |
| 2,3-dichloro | Me | 2-hydroxyethyl |  |  | 95/10; 77/3.0; 62/1.0; 14/0.1 |
| 2,3-dichloro | H | 2-acetoxyethyl |  |  | 72/1.0; 62/0.3; 18/0.1 |
| 2,3-dichloro | H | 2-hydroxyethyl |  |  | 56/10; 0/1.0 |
| 2,3-dichloro | H | cyclopropylmethyl |  |  |  |
| 2,3-dichloro | H | cyclopropylmethyl |  |  | 93/10; 86/3.0; 17/0.01 |

Structure (bottom):

A dihydropyridine with a 2-sulfonylphenyl group bearing $R_4$-NH substituent, and the $R_3$/R_2/CH3 substitution pattern as above.

| R3 = Phenyl Substitution | R4 | R2 | P#166 Nit. Binding | P#176 Trach % INHB/μM | P#176 Aorta % INHB/μM |
|---|---|---|---|---|---|
| 2,3-dichloro | CHO | ethyl |  | 73/2.0; 35/0.3; 38/0.01 | 74/1.0; 50/0.1; 33/0.01 |

The assay for inhibition of nitrendipine binding is performed using the following procedure:

Female, New Zealand white rabbits (1-2 kg) are sacrificed by cervical dislocation, and the heart is immediately removed, cleaned and chopped into small pieces. The tissue is homogenized in 5×volume of 0.05M Hepes buffer, pH 7.4. The homogenate is centrifuged at 4000×g for 10 minutes, and the supernatant is recentrifuged at 42,000×g for 90 minutes. The resulting membrane pellet is resuspended (0.7 ml/g weight) in 0.05M Hepes, pH 7.4 and stored at 70° C. until used. Each tube of the binding assay contains $^3$H-nitrendipine (0.05-0.50 nM), buffer, membranes (0.10 ml), and test compound in a total volume of 1.0 ml. After 90 minutes at 4° C., the bound nitrendipine is separated from the unbound by filtration on Whatman GF/C filters. After rinsing, the filters are dried and counted in a liquid scintillation counter.

Non-specific binding of $^3$H-nitrendipine (that amount bound in the presence of excess unlabelled nitrendipine) is subtracted from the total bound to obtain specifically bound radiolabeled nitrendipine. The amount of specifically bound nitrendipine in the presence of a test compound is compared to that amount bound in the absence of a compound. A percent displacement (or inhibition) can then be obtained.

The test for inhibition of calcium dependent smooth muscle contraction is determined according to the following procedure:

The trachea and the aorta from dogs sacrificed by excess KCl injection are stored overnight at 4° C. in oxygenated Krebs-Henseleit buffer. Tracheal rings, one cartilage segment wide (5-10 mm), are cut starting from the bronchial end. Rings of aorta tissue of the same width are also prepared. After cutting the cartilage, the trachealis muscle tissue and the aorta tissue are suspended in oxygenated Krebs-Henseleit buffer at 37° C. in a 25 ml tissue bath. After a 60-minute equilibration period, the tissues are challenged with 10 μM carbachol. After 5 minutes, the tissues are rinsed and allowed to rest 50 minutes. The tissues are then challenged with 50 mM KCl and, after 30 minutes, the contractions are quantitated. The tissues are then rinsed and reequilibrated for 50 minutes. Test compounds are then added for 10 minutes, and the tissue is rechallenged with 50 mM KCl. After 30 minutes, the contraction is recorded and used to determine the % inhibition of control.

The percent inhibition of smooth muscle contraction is calculated from response data before and after drug treatment.

$$\% \text{ inhibition} = 100 - 100 \left[ \frac{\text{peak response after drug treatment}}{\text{peak response before drug treatment}} \right]$$

What is claimed is:
1. A compound of the formula

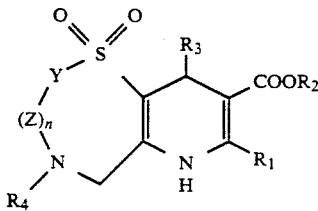

wherein
Y and Z are $CH_2$ or together Y and Z form an ortho fused phenyl ring;
$R_1$ is hydrogen, amino, $C_1$-$C_8$ straight or branched chain alkyl, trifluoromethyl or alkoxymethyl;
$R_2$ is $C_1$-$C_8$ straight or branched chain alkyl, substituted alkyl, benzyl, 3-piperidyl, N-substituted 3-piperidyl or N-substituted 2-pyrrolidinyl methylene;
wherein said N-substituted 3-piperidyl and said substituted 2-pyrrolidinyl methylene are substituted with $C_1$-$C_8$ straight or branched chain alkyl or benzyl, and said substituted alkyl is substituted with $C_1$-$C_8$ alkoxy, alkanoyloxy, phenylacetyloxy, benzoyloxy, hydroxy, halogen, p-tosyloxy, mesyloxy, amino or $NR_5N_6$;
$R_3$ is 2-pyridyl, 3-pyridyl, 2-thienyl, 3-thienyl, 2,1,3-benzoxadiazolyl, 2,1,3-benzthiadiazolyl or substituted phenyl;
wherein said substituted phenyl is substituted at any of positions 2-6 with hydrogen, $C_1$-$C_8$ straight or branched chain alkyl, $C_1$-$C_8$ alkoxy, cyano, $C_1$-$C_8$ alkylthio, difluoromethoxy, difluoromethylthio, $C_1$-$C_8$ alkylsulfonyl, halogen, nitro or trifluoromethyl;
$R_4$ is hydrogen, $C_1$-$C_8$ straight or branched chain alkyl, $C_3$-$C_7$ cycloalkyl, phenyl, benzyl, substituted benzyl, formyl, acetyl, t-butyloxy carbonyl, propionyl, substituted alkyl or $R_7CH_2C=O$;
wherein said substituted benzyl is substituted with halogen, trifluoromethyl, $C_1$-$C_8$ straight or branched chain alkyl or $C_1$-$C_8$ alkoxy, and said substituted alkylis substituted with amino, dialkyl amino, $C_1$-$C_8$ alkoxy, hydroxy or halogen;
$R_5$ and $R_6$ are the same or different and are hydrogen, $C_1$-$C_8$ straight or branched chain alkyl, $C_3$-$C_7$ cycloalkyl, phenyl, benzyl, phenethyl or $R_5$ and $R_6$ together are a heterocyclic ring selected from the group consisting of piperidino, pyrrolidino, morpholino, thiomorpholino, piperazino and an N-substituted derivative of said heterocyclic rings;
wherein said N-substituted heterocyclic ring is substituted with hydrogen, $C_1$-$C_8$ straight or branched chain alkyl, benzyl, benzhydryl, phenyl or substituted phenyl;
wherein said substituted phenyl is substituted with hydrogen, $C_1$-$C_8$ straight or branched chain alkyl, $C_1$-$C_8$ alkoxy, halogen, nitro or trifluoromethyl;
$R_7$ is amino, dialkyl amino, $C_1$-$C_8$ alkoxy, hydroxy or halogen; and
n is 1 to 4;
and optical antipodes or pharmaceutically acceptable salts thereof.

2. The compound of claim 1 wherein
$R_1$ is methyl;
$R_2$ is ethyl or substituted alkyl;
$R_3$ is substituted phenyl;
$R_4$ is hydrogen, $C_1$-$C_8$ straight or branched chain alkyl, benzyl, formyl, t-butyloxycarbonyl or $R_7CH_2C=O$;
$R_7$ is amino; and
n is 1.

3. The compound of claim 1 selected from the group consisting of
a. 2-(N-benzyl-N-methylamino)ethyl 9-(2,3-dichlorophenyl)-1,1-dioxo-2,3,4,5,6,9-hexahydro-7-methyl-pyrido[2,3-f][1,4]-thiazepine-8-carboxylate;
b. 2-(N-benzyl-N-methylamino)ethyl 9-(2,3-dichlorophenyl)-4,7-dimethyl-1,1-dioxo -2,3,4,5,6,9-hexahydropyrido[2,3-f][1,4]-thiazepine-8-carboxylate;
c. Ethyl 9-(2,3-dichlorophenyl)-1,1-dioxo -2,3,4,5,6,9-hexahydro-7-methyl-pyrido[2,3-f][1,4]thiazepine-8-carboxylate;
d. Ethyl 9-(2,3-dichlorophenyl)-1,1-dioxo-4-ethyl-2,3,4,5,6,9-hexahydro-7-methyl-pyrido -[2,3-f][1,4]thiazepine-8-carboxylate;
e. Ethyl 9-(2,3-dichlorophenyl)-4,7-dimethyl,1-dioxo-2,3,4,5,6,9-hexahydropyrido[2,3-f]-[1,4]thiazepine-8-carboxylate;
f. Ethyl 4,7-dimethy-1,1-dioxo-2,3,4,5,6,9-hexahydro-9-(2,3,4,5,6-pentafluorophenyl) -pyrido [2,3-f][1,4]thiazepine-8-carboxylate;
g. Ethyl 1,1-dioxo-2,3,4,5,6,9-hexahydro-7-methyl-9-(2,3,4,5,6-pentafluorophenyl) -pyrido[2,3-f][1,4]thiazepine-8-carboxylate;
h. Ethyl 1,1-dioxo-4-ethyl-2,3,4,5,6,9-hexahydro -7-methyl-9-(3-nitrophenyl)-pyrido[2,3-f][1,4]thiazepine-8-carboxylate;
i. Ethyl 4-(2,3-dichlorophenyl)-5,5-dioxo-10-formyl-2-methyl-1,4,10,11-tetrahydropyrido -[3,2-b][1,5]benzothiazepine-3-carboxylate;
j. 2-Acetoxyethyl 9-(2,3-dichlorophenyl)-4,7-dimethyl-1,1-dioxo-2,3,4,5,6,9-hexahydropyrido[2,3-f][1,4]thiazepine-8-carboxylate;
k. 2-Pivaloyloxyethyl 9-(2,3-dichlorophenyl) -4,7-dimethyl-1,1-dioxo-2,3,4,5,6,9-hexahydropyrido[2,3-f][1,4]thiazepine-8-carboxylate;

l. Ethyl 4-(2,3-dichlorophenyl)-2,10-dimethyl-5,5-dioxo-1,4,10,11-tetrahydropyrido[3,2-b][1,5]benzothiazepine-3-carboxylate;

m. 2-(N-benzyl-N-methylamino)ethyl 4-(2,3-dichlorophenyl)-2,10-dimethyl-5,5-dioxo-1,4,10,11-tetrahydropyrido[3,2-b][1,5]-benzothiazepine-3-carboxylate;

n. 2-(N,N-dibenzylamino)ethyl 4-(2,3,dichlorophenyl)-4,7-dimethyl-1,1-dioxo-2,3,4,5,6,9-hexahydropyrido[2,3-f][2,4]thiazepine-8-carboxylate;

o. 2-(n-benzyl-N-methylamino)ethyl 4-(2,3-dichlorophenyl)-4-ethyl-1,1-dioxo-2,3,4,5,6,9-hexahydro-7-methyl-pyrido[2,3-f][1,4]thiazepine-8-carboxylate; and p. (N-benzyl-2-pyrolidinyl)methyl 9-(2,3-dichlorophenyl)-4,7-dimethyl-1,1-dioxo-2,3,4,5,6,9-hexahydropyrido[2,3-f][1,4]-thiazepine-8-carboxylate.

* * * * *

UNITED STATES PATENT AND TRADEMARK OFFICE
CERTIFICATE OF CORRECTION

PATENT NO. : 5,075,440
DATED : December 24, 1991
INVENTOR(S) : David J. Wustrow, et. al.

It is certified that error appears in the above-indentified patent and that said Letters Patent is hereby corrected as shown below:

Col. 1, line 65, change "trifluooomethyl" to --trifluoromethyl--

Col. 18, line 1, change "alkylis" to --alkyl is--

Signed and Sealed this

Fifteenth Day of June, 1993

Attest:

MICHAEL K. KIRK

*Attesting Officer*    Acting Commissioner of Patents and Trademarks